United States Patent [19]
Weiss

[11] Patent Number: 5,997,582
[45] Date of Patent: Dec. 7, 1999

[54] HIP REPLACEMENT METHODS AND APPARATUS

[76] Inventor: James M. Weiss, 14804 Spring Meadows Dr., Darnestown, Md. 20874

[21] Appl. No.: 09/071,203

[22] Filed: May 1, 1998

[51] Int. Cl.$^6$ ........................................................ A61F 2/36
[52] U.S. Cl. ................................. 623/23; 623/18; 606/89
[58] Field of Search ................................. 623/16, 18, 22, 623/23; 606/77, 86, 89, 92; 128/898

[56] References Cited

U.S. PATENT DOCUMENTS

| | | | |
|---|---|---|---|
| 4,627,853 | 12/1986 | Campbell | 623/23 |
| 4,865,604 | 9/1989 | Rogozinski | 623/23 |
| 5,108,404 | 4/1992 | Scholten et al. | 606/94 |
| 5,258,603 | 11/1993 | Lawes et al. | 623/22 |
| 5,556,429 | 9/1996 | Felt | 623/16 |
| 5,591,232 | 1/1997 | Rahimi et al. | 623/16 |
| 5,716,413 | 2/1998 | Walter et al. | 623/16 |
| 5,725,593 | 3/1998 | Caracciolo | 623/23 |
| 5,827,287 | 10/1998 | Reiley et al. | 606/86 |
| 5,827,289 | 10/1998 | Reiley et al. | 606/986 |

FOREIGN PATENT DOCUMENTS 560040  3/1975  Switzerland ............................. 623/22

*Primary Examiner*—Bruce E. Snow
*Attorney, Agent, or Firm*—Burns, Doane, Swecker & Mathis, L.L.P.

[57] ABSTRACT

A hip replacement is performed by separating a femoral head from a femoral neck in a patient's body, fragmenting of the femoral head and removing the fragments from the body, and molding in-situ in the body a neo femoral head joined to the femoral neck. The molding is performed by inserting a molding device, formed of bioabsorbable material, through a hole formed through the femoral head and the femoral neck. The molding device includes an expandable balloon which is expanded by the introduction of molding material, whereby the balloon forms the shape of the neo femoral head.

16 Claims, 13 Drawing Sheets

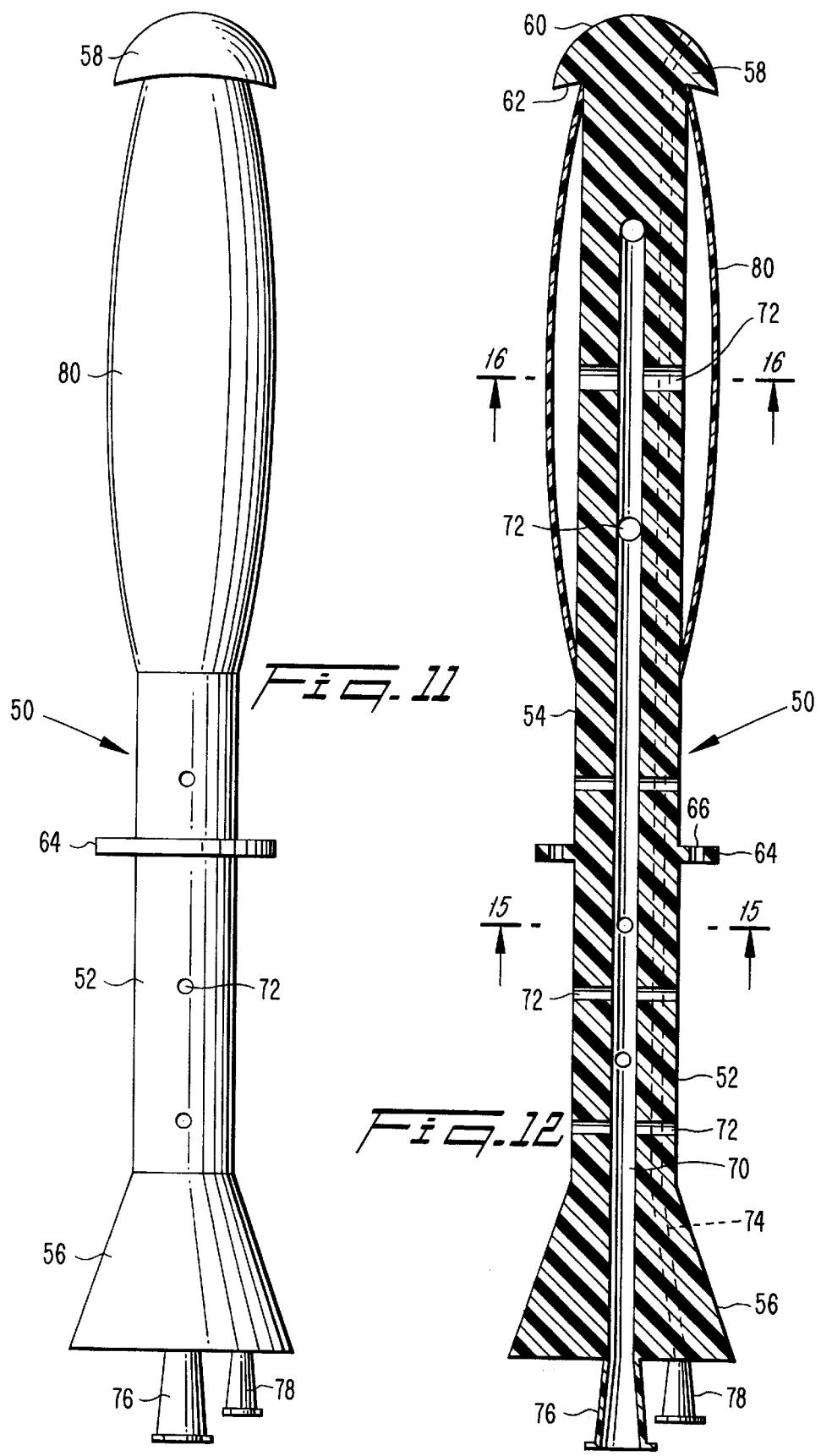

HIP REPLACEMENT METHODS AND APPARATUS

BACKGROUND OF THE INVENTION

The present invention relates to methods and apparatus for performing a hip replacement.

Hip replacement surgery, pioneered in the early 1960's, has been characterized by the substitution of the degenerated joint with prosthetic components, typically formed of polyethylene and metal alloys. These are affixed to the underlying bone immediately at the time of surgery by the use of bone cement or by coating or texturing the components in such a manner as to allow the surrounding bone to eventually grow into the surface. However subsequent loosening of the prosthesis, regardless of the method of fixation, has been a well documented complication of the procedure. Additionally, this loosening can become clinically symptomatic requiring revision surgery. This problem is especially concerning in younger individuals who have undergone joint replacement, as their functional demands are often higher than in older individuals and their expected lifespan may be in excess of the anticipated functional life of the replacement.

Further study of the problem of long term prosthetic loosening has suggested that the common underlying pathway of failure for cemented and uncemented prostheses involves the generation of particulate debris. That is, particles of polyethylene, submicron in size, are generated by the articulation of the two prosthetic components during motion. It is estimated that some 500,000 submicroscopic polyethylene particles are produced with each individual step that a patient takes, with as many as 1,000,000 cycles or steps per year. It has been postulated that this debris creates not only third body wear of the components, but also produces an inflammatory reaction in certain individuals resulting in the release of degradative enzymes. These enzymes can ultimately lead to a breakdown of the bone/cement or bone/prosthesis interface.

Consequently, significant effort has been directed toward reducing the production of such particles, mainly by improving the biomechanical properties of the polyethylene through manufacturing and processing techniques. As well, the use of ultra-low friction ceramics has been tried in clinical practice toward this end, however cases reports of early prosthetic fractures necessitating revision surgery has curtailed their use. A reemergence of trials of metal-on-metal articulations has also recently appeared, but no long-term data on these is available as of yet, leaving the problem of particulate debris and loosening as the single and most significant unsolved problem facing joint replacement surgeons today.

Therefore, it would be desirable to provide hip replacement methods and techniques which eliminate or alleviate the above described problems.

SUMMARY OF THE INVENTION

That object is achieved by the present invention which involves a hip replacement method comprising the steps of:

A) separating a femoral head from a femoral neck in a patient's body;

B) removing the femoral head from the body; and

C) molding in-situ in the body a neo-femoral head joined to the femoral neck.

Prior to step A, a pilot hole is preferably formed through the femoral neck and the femoral head starting from the lateral cortex. Step C preferably comprises inserting into the hole a molding device for defining a shape of the neo femoral head. The device is formed of bioabsorbable materials. A molding substance is inserted into and around the device, preferably into an expandable balloon portion of the device, whereby the balloon is expanded. Thereafter, the molding substance is allowed to set.

The invention also pertains to the molding device for the in-situ molding of a neo-femoral head during a hip replacement procedure. The molding device comprises an elongated body formed of bioabsorbable materials and having front and rear ends and a passage formed therein for communicating the rear end with an outer peripheral surface of the body. The device also includes a balloon formed of bioabsorbable material and mounted on the body adjacent a front end thereof. The passage communicates with the outer peripheral surface at a location inside of the balloon and at a location outside of the balloon.

BRIEF DESCRIPTION OF THE DRAWING

The objects and advantages of the invention will become apparent from the following detailed description of a preferred embodiment thereof in connection with the accompanying drawings, in which like numerals designate like elements and in which:

FIG. 11 is a side view of the molding device according to the present invention;

FIG. 12 is a longitudinal sectional view taken through the molding device of FIG. 11;

DETAILED DESCRIPTION OF A PREFERRED EMBODIMENT OF THE INVENTION

Figure 1:
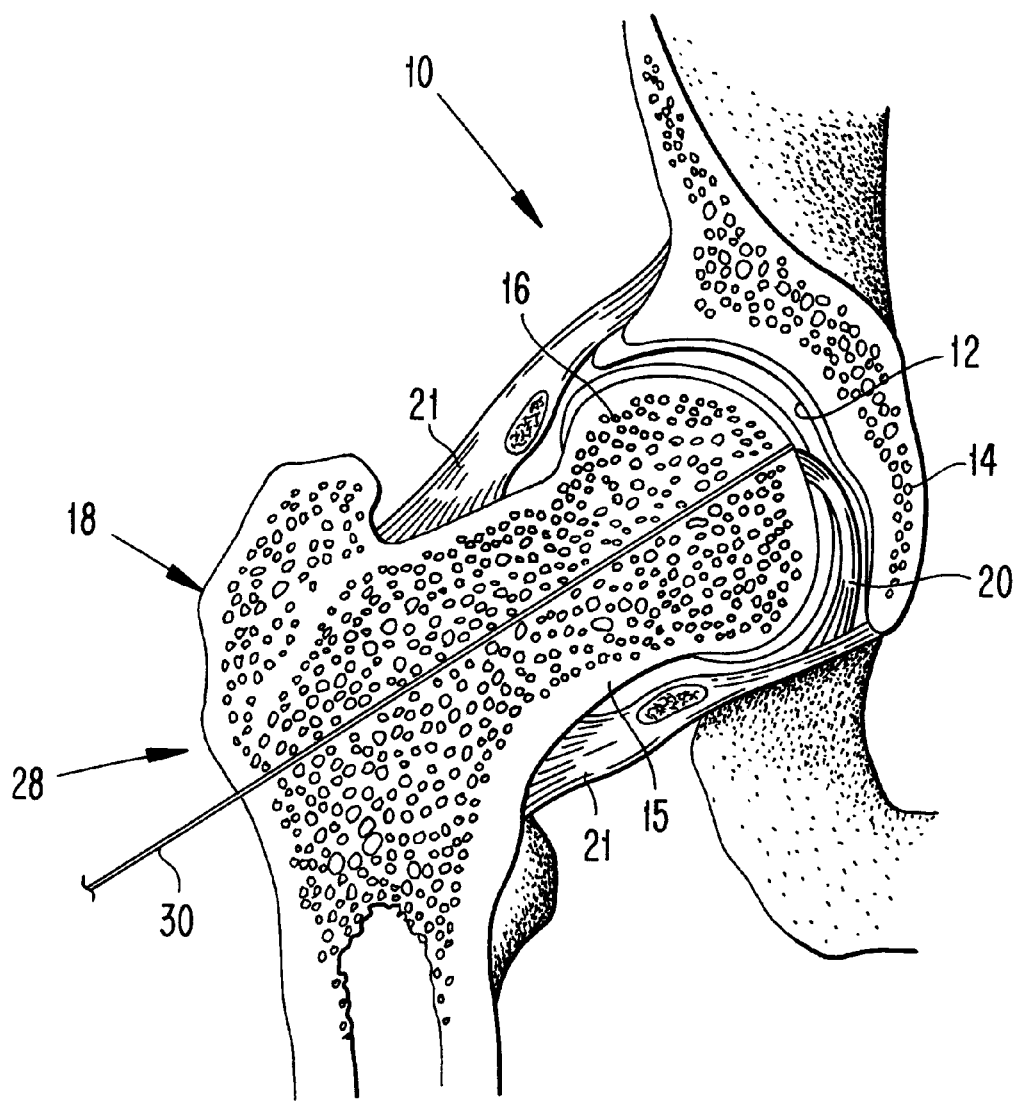
FIG. 1 is a sectional view taken through a hip joint after a guide wire has been inserted centrally through the femoral neck and femoral head of the joint.
Figure 17:
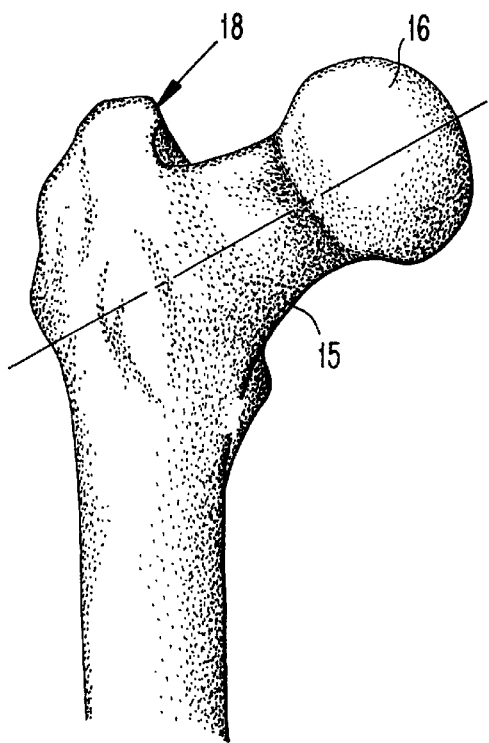
FIG. 17 is a side view of the femur.
Figure 18:
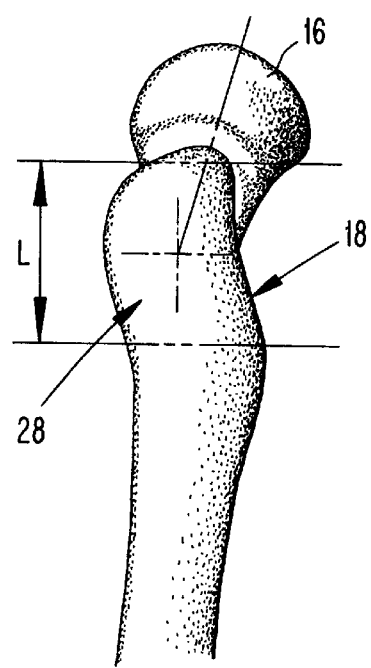
FIG. 18 is a side view of the femur depicting the lateral cortex of the femur.

FIG. 1 depicts, prior to a replacement procedure, a ball-and-socket hip joint 10. The socket is comprised of a cup-shaped cavity formed by the acetabulum 14, and the ball is formed by the head 16 of a femur. The head 16 projects from a neck 15 of the femur and is joined to the socket by a ligamentum teres attachment and joint capsule 21. The femur is also depicted in FIGS. 17 and 18.

Prior to performing a hip replacement procedure according to the present invention, an arthroscopy of the patient's ipsilateral knee is performed about three weeks prior to the planned procedure. Using standard arthroscopic techniques, a harvest of a cartilage graft is procured from the femoral condyle, where the non articular portion of the femoral condyle is most accessible. The harvested cells are stored and prepared according to the protocol as outlined in the NEJM 10/94 331 p 889.

To perform the hip replacement procedure, the patient is placed on a radiolucent fracture table in a supine position as would be typically used to address an intertrochanteric hip fracture. The ipsilateral foot is well padded and then placed in a traction boot. A well leg holder is used for the other leg. A six centimeter incision is made at the inferior border of the greater trochanter in the midline of the lateral femur, to expose a length L of the lateral cortex 28 of the femur (see FIG. 18), similar to the incision made when fixing an intertrochanteric hip fracture.

Under fluoroscopic control, a standard guide wire 30 found in any standard hip screw set is passed centrally through the femoral neck 15 and head 16 (see FIG. 1). Proper centering should be confirmed on AP and Lateral views. Approximate centering, which is acceptable in fixing hip fractures is not adequate and the wire should be repeatedly passed until it is dead center on both views.

Figure 2:
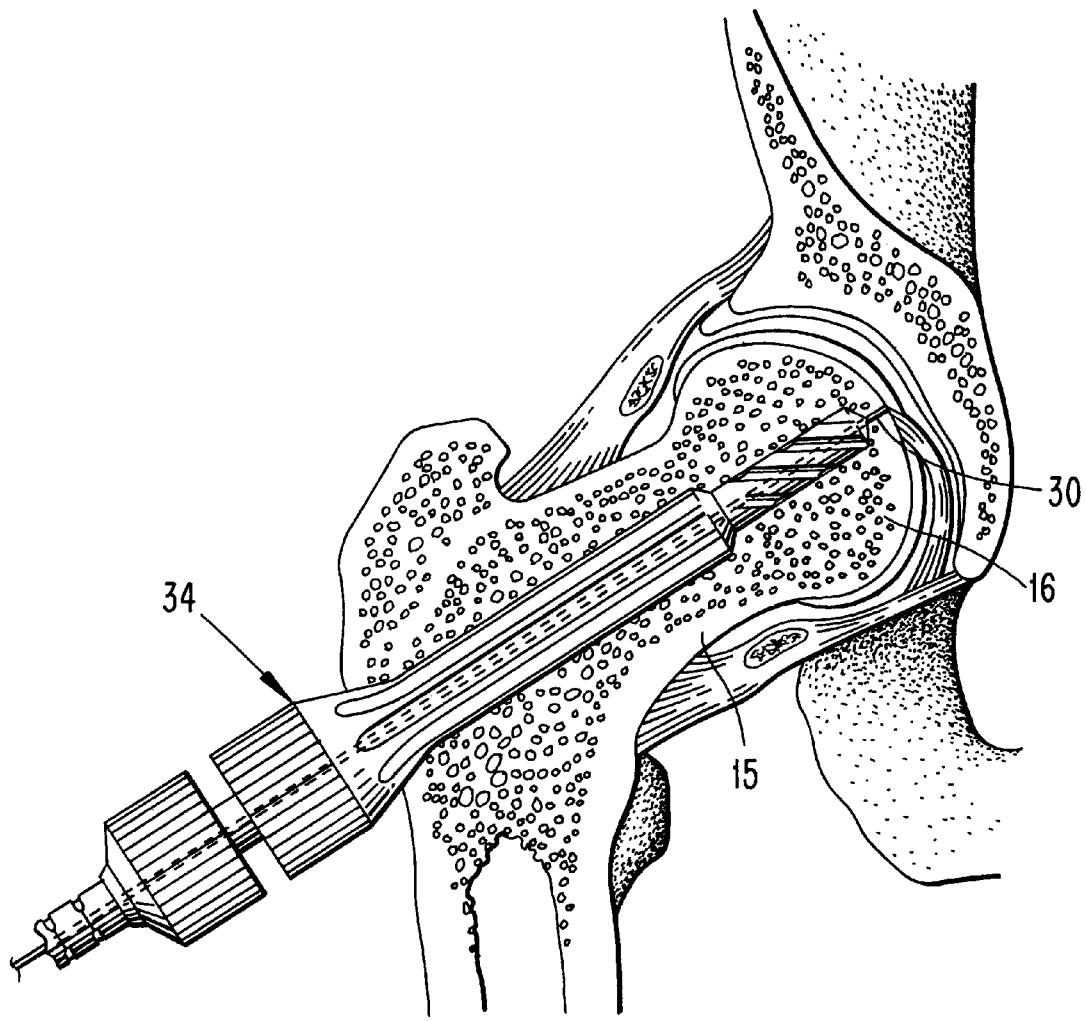
FIG. 2 is a view similar to FIG. 1 after a drill has bored out the femoral neck and femoral head.
Figure 3:
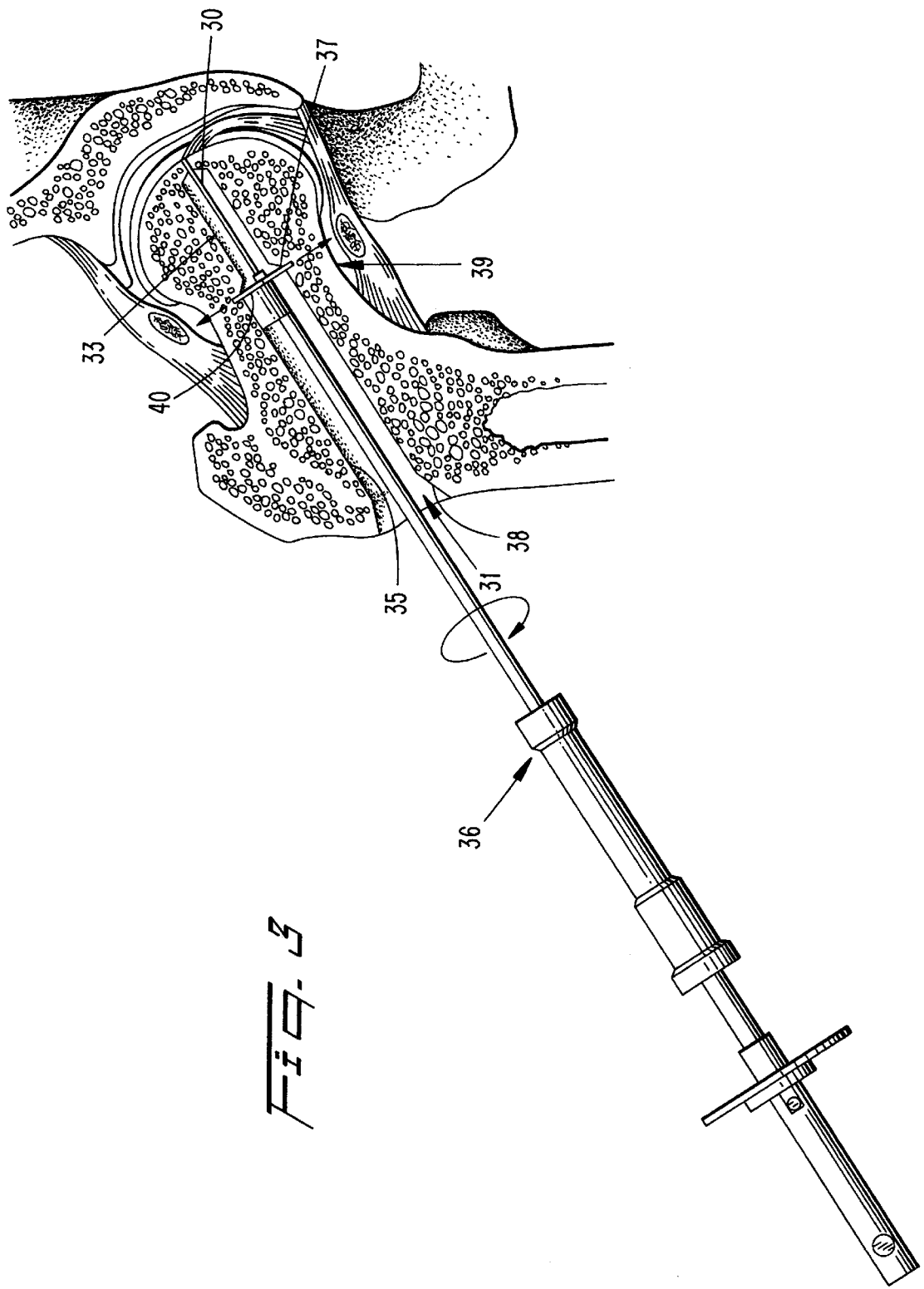
FIG. 3 is a view similar to FIG. 2, depicting a saw in the process of severing the femoral head from the femoral neck.

Once it has been confirmed that the guide wire 30 has been properly centered, a standard triple reaming drill 34 is fed along the guide wire 30 to bore a hole 31 through the femoral neck 15 and head 16 (see FIG. 2). A description of such a step may be found in *The Dynamic Hip Screw Implant System* by Regozzoni, Rüedi, Winquist, and Allgöwer, 1985 Springer-Verlag Berlin, Heidelberg, New York, Tokyo. A front portion of the drill cuts a 10 mm diameter portion 33 of the hole 31 (FIG. 3), and a rear portion of the drill cuts a 12 mm diameter portion 35 of the hole 31. An intersection 37 of the two bore, which coincides with the junction 39 of the femoral neck 15 and head 16, is flared by the drill. Also, the extreme outer end 38 of the bore 35 at the lateral cortex is flared by the drill to about 22 mm.

Figure 4:
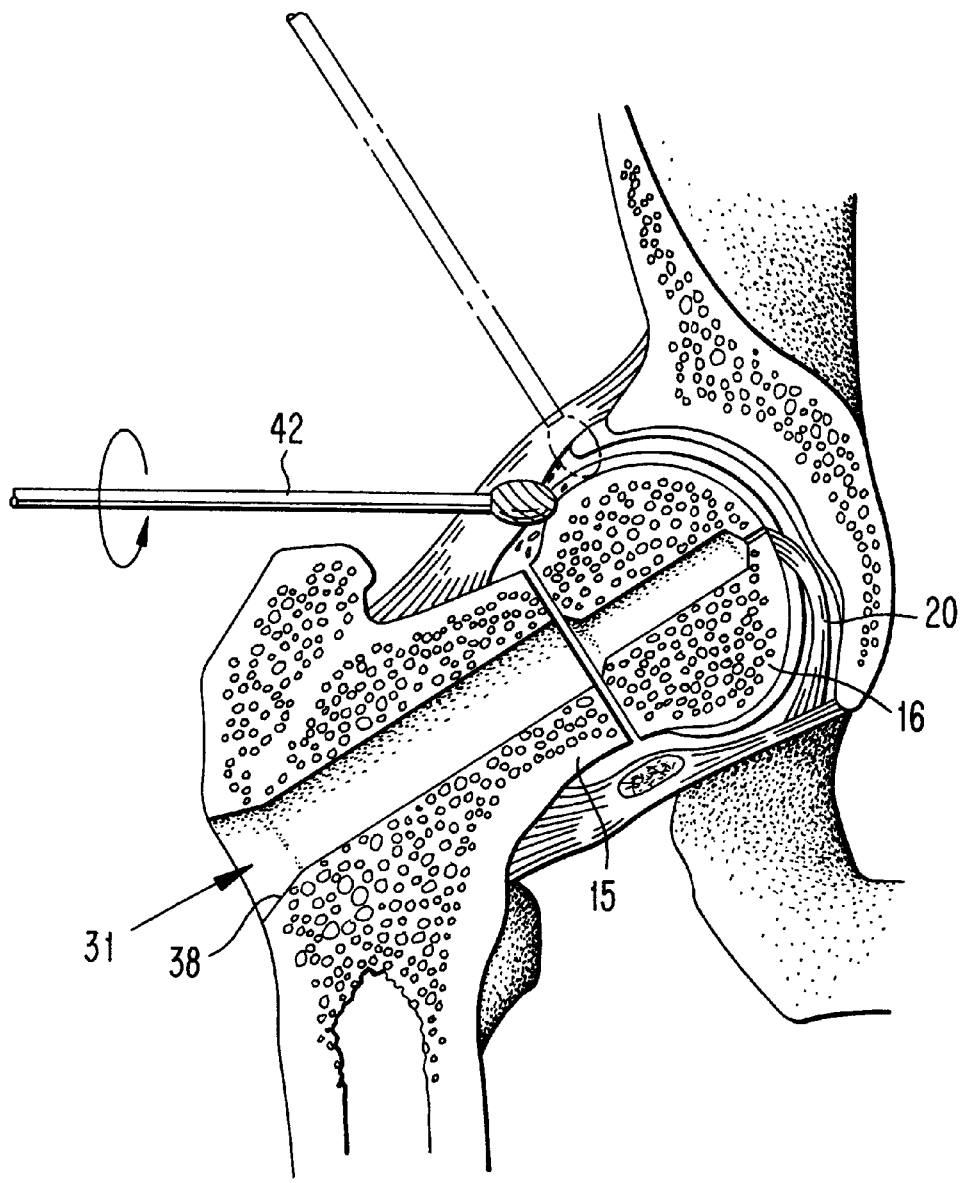
FIG. 4 is a view similar to FIG. 3 after the saw has been removed and a burr has been inserted to fragment the femoral head.

A standard OEC femoral shortening saw 36 is then fed along the guide wire 30 until the blade 40 of the saw reaches the flare 37 at the junction between the femoral neck and head. Under floro control this position is confirmed on two views. The blade 40 of the saw is then gradually deployed until the neck has been fully cut, disengaging the femoral head (see FIG. 4). The head 16 is now free floating in the joint except for its ligamentum teres attachment 20. Then, the guide wire 30 is removed, and standard anterior arthroscopic portals are exploited to introduce an arthroscope and a grasper (not shown), as well as a conventional high speed aggressive flame burr 42 for fragmenting the femural head 16. The grasper is used to stabilize the head 16 while the flame burr is fragmenting it. The burr makes only a very small puncture in the capsule 21. The "bone dust" representing the formal femoral head is carried away with the outflow fluid through the hole 31.

Figure 5:
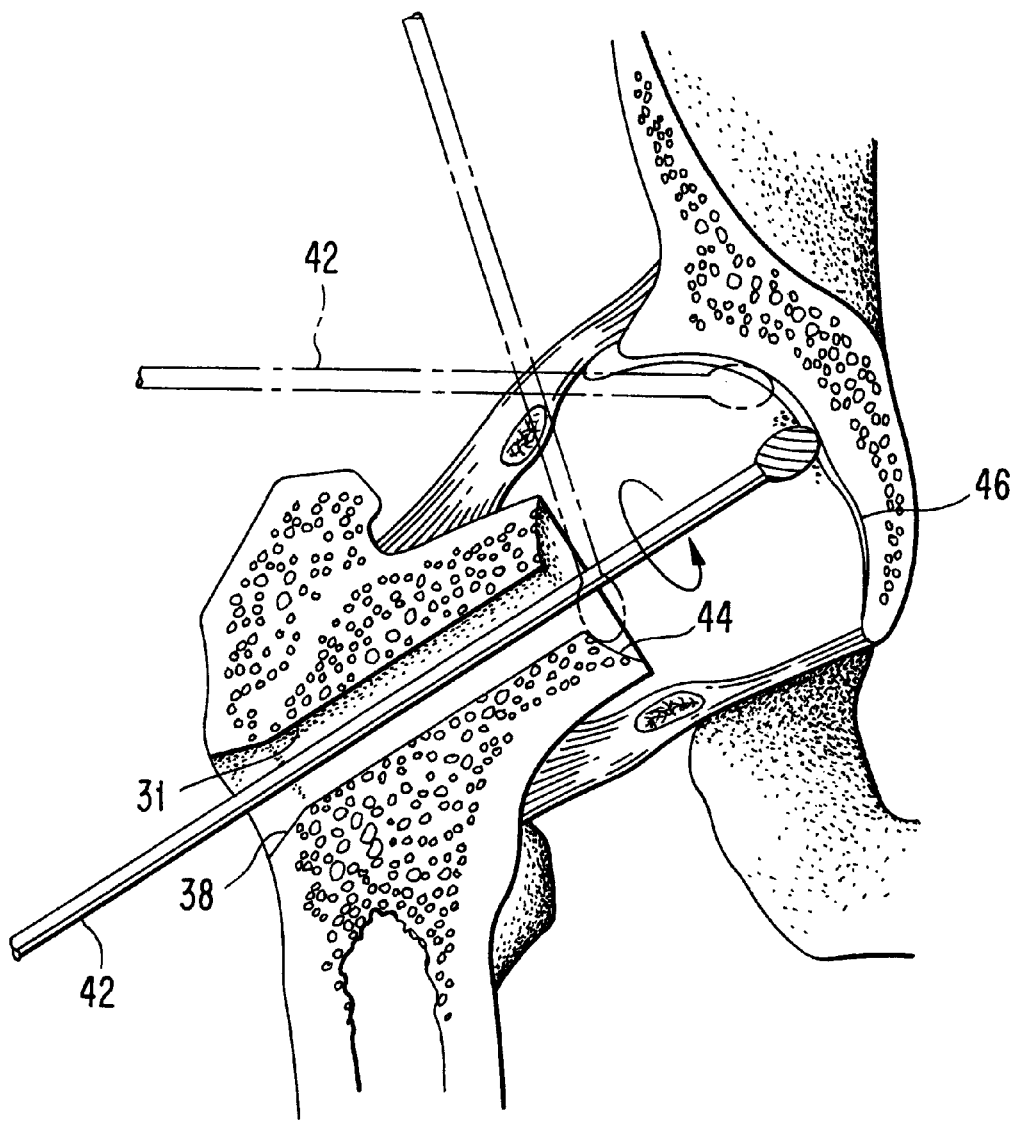
FIG. 5 is a view similar to FIG. 4 after the burr has been inserted through the hole to denude the degenerated cartilage of the acetabulum.

Once the head 16 has been fragmented, the burr 42 is maneuvered to cut a concave recess 44 in the end of the femural neck 15 (FIG. 5). Then, the burr 42 is placed through the hole 31 to enable the degenerated cartilage 46 of the acetabulum to be denuded (see also FIG. 5).

If desired, a Coherent Holmium:YAG laser could be introduced into the joint through the previously established arthroscopic portholes. Using a 2.0 joule 40 htz setting, any remaining acetabular cartilage could be vaporized.

At this point, a neo-femoral head will be reconstituted through the use of a molding device 50 depicted in FIGS. 12–17. The molding device 50 comprises a body 52 formed of a suitable bioabsorbable material such as polylactic or polyglycolic acid. The body 52 includes a cylindrical main section 54, having a flared rear end 56 (the angle of the flare matching the flare angle of the end 38 of the hole 31), and a front tip 58 having a convex, spherically curved front surface 60 of larger diameter than the diameter of the main section 54. Thus, the front tip 58 forms a rearwardly projecting shoulder 62.

The main section 54 includes a lateral flange or centering bushing 64 located intermediate the front and rear ends, and having an outer diameter corresponding to the diameter of the hole 31 and to the diameter of the front surface 60. Axial through-holes 66 are formed in the bushing 64. The length of the main section can vary, depending on the length of the femoral neck 15.

An axial central passage 70 extends along the axis of the body 52 from the rear end thereof and terminates short of the front tip 58. Lateral passages 72 project outwardly from the central passage 70 and extend through the outer peripheral surface of the body 62.

A secondary passage 74 extends completely through the body 52 from the rear end to the front tip, preferably parallel to the axis of the body 52. The passages 70 and 74 terminate rearwardly in the form of tapered (frustoconical) inlet ports 76, 78, respectively, that are integral with the body 52.

Attached to the body 52 by means of a biocompatible adhesive is an expandable balloon 80 which will define the shape of a neo-femoral head. The balloon 80 is formed of a suitable bioabsorbable material which can be expanded and eventually absorbed by the body. For example, the balloon could be formed of Marlex Mesh or a cloth woven of bioabsorbable suture material. The balloon need not be water-tight or air tight, but need only be able to retain a molding substance, such as conventional fracture grout, which will be employed to expand the balloon (as will be hereinafter described). To that end, the balloon surrounds some of the lateral passages 72.

Figure 6:
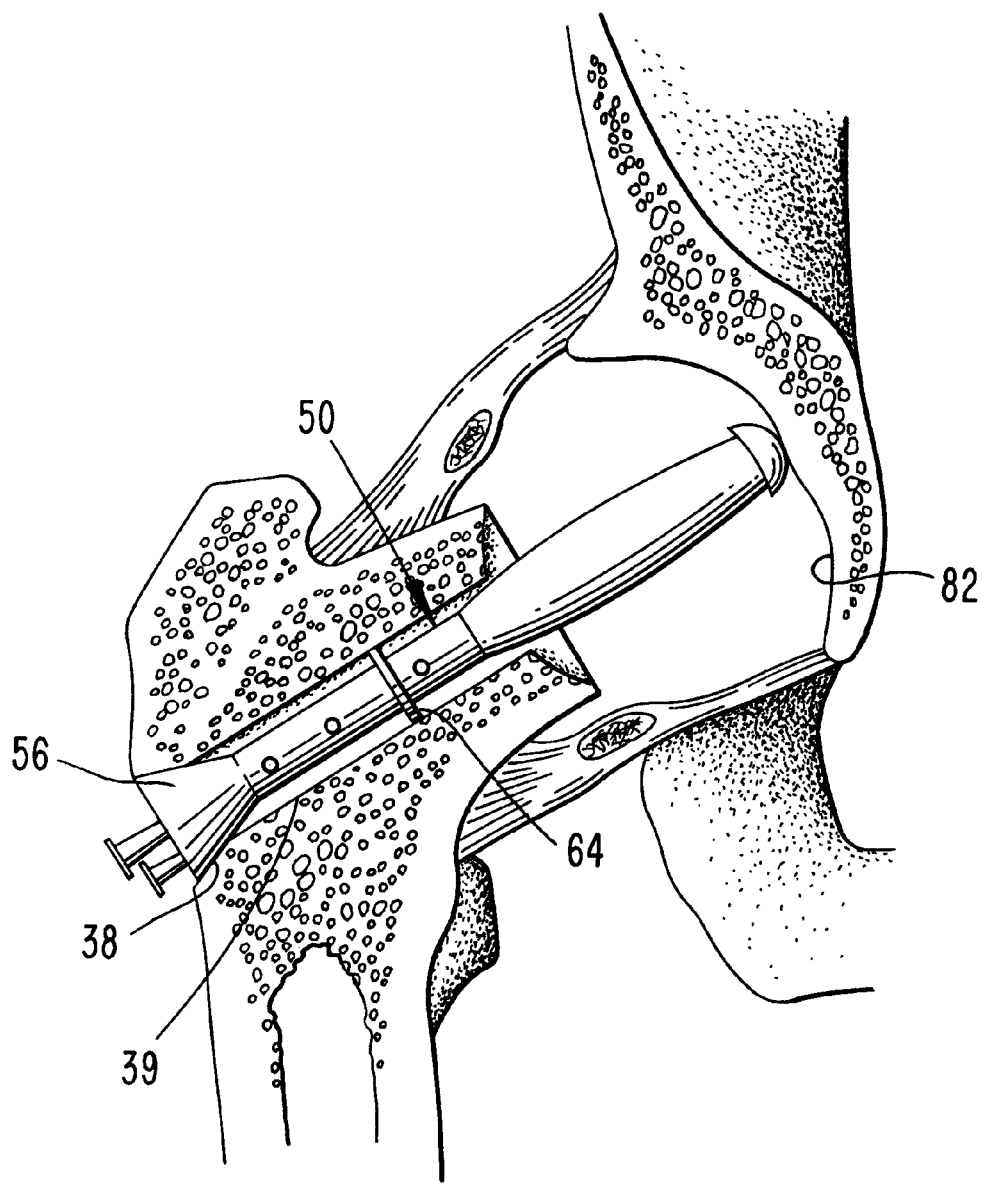
FIG. 6 is a view similar to FIG. 5 after a molding device has been inserted through the drilled hole.

The manner of utilizing the molding device 50 to mold, in-situ, a neo femoral head is depicted in FIGS. 6–9. As shown in FIG. 6, the device 50 is inserted through the hole 31 until the flared end 56 of the body 52 bears snugly against the flared end 38 of the hole 31. The device 50 is stabilized and centered within the hole 31 by the bushing 64 which bears against the wall of the hole 31. A body 52 of suitable length will have been selected for use to ensure that the front tip 58 bears against the socket wall 82 of the acetabuhum as shown in FIG. 6. A fluoroscopic image is then taken to determine that the device has been properly positioned.

Figure 7:
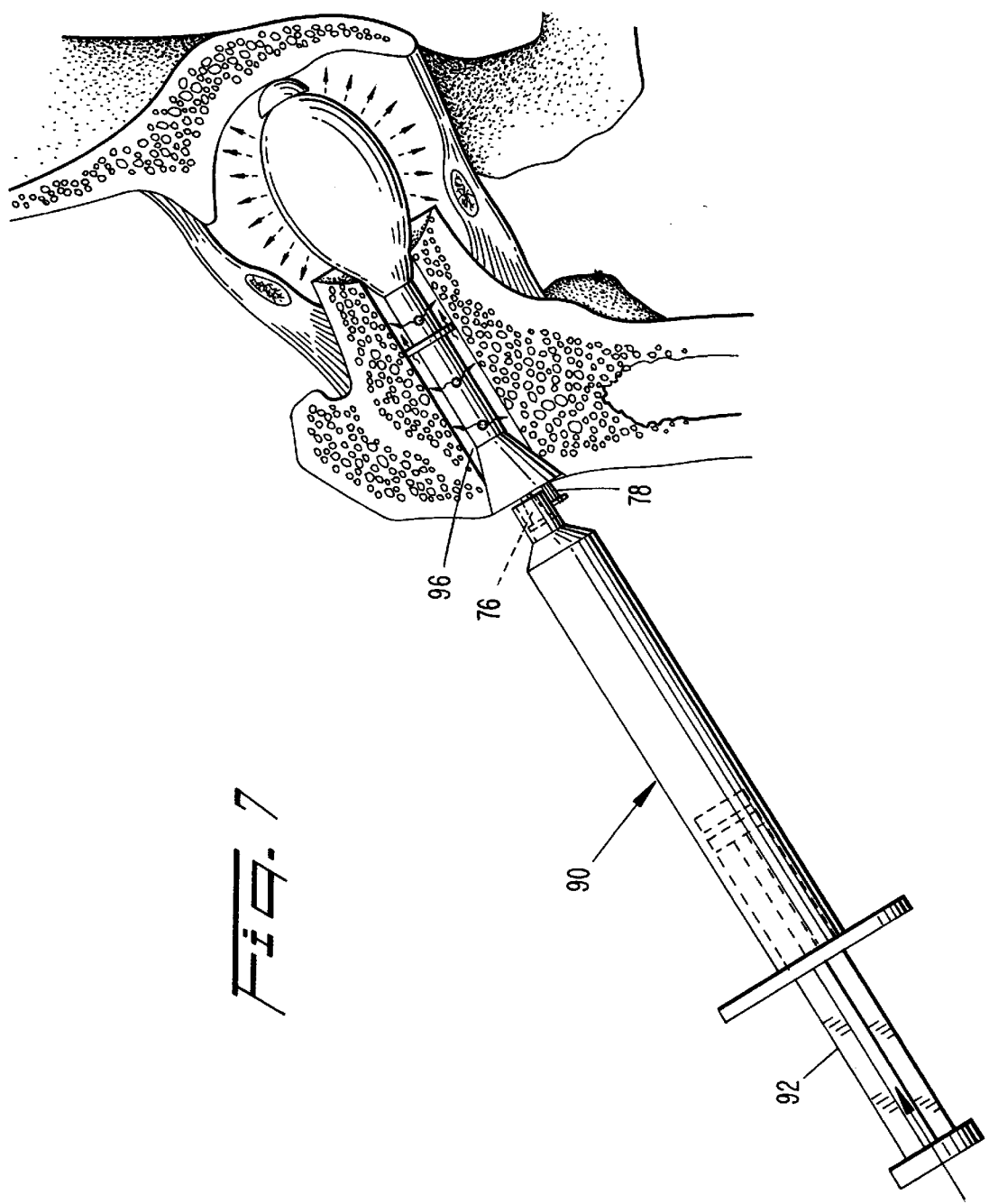
FIG. 7 is a view similar to FIG. 6 as molding compound is being introduced through the molding device to expand a balloon of the molding device.
Figure 8:
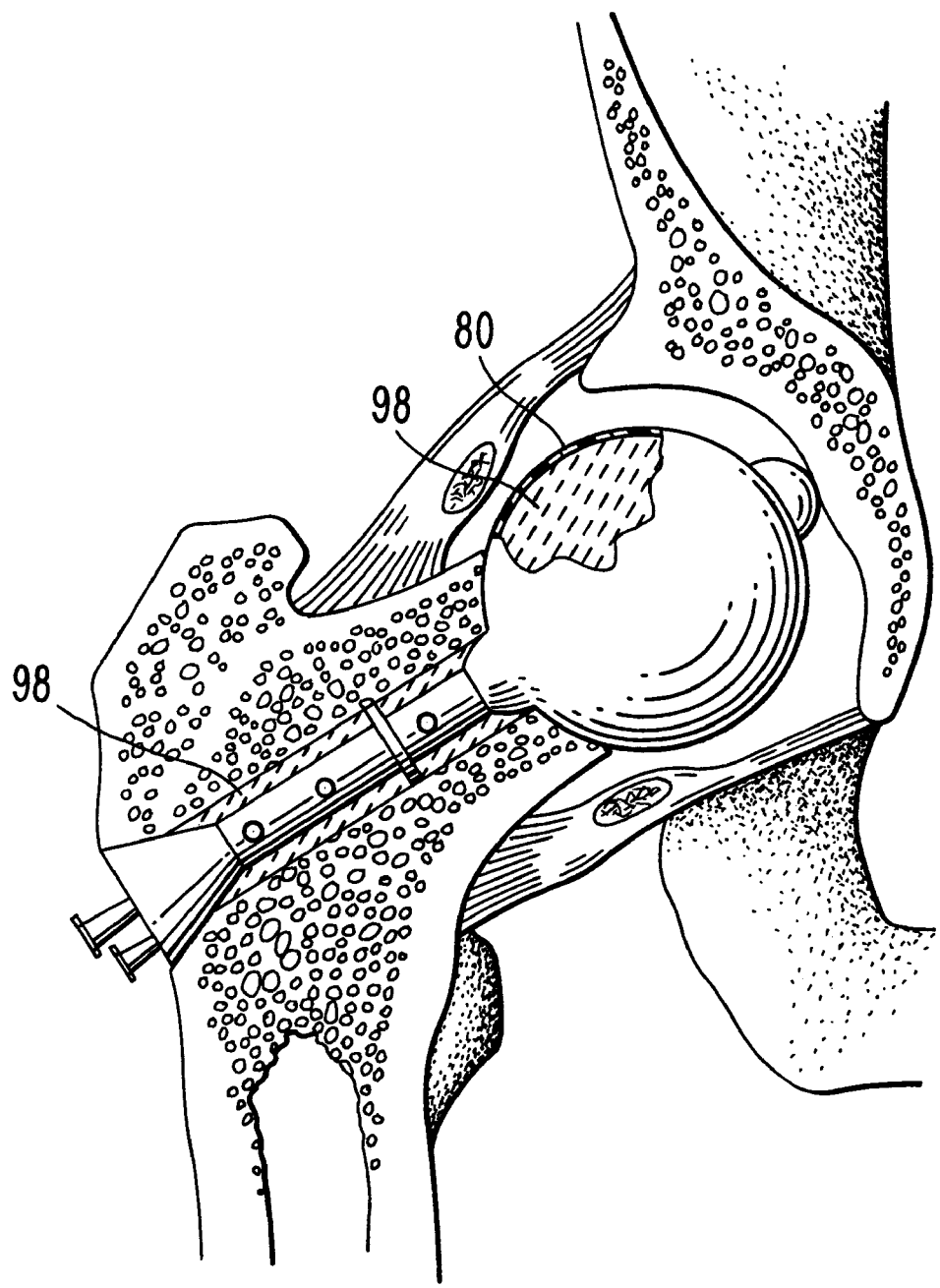
FIG. 8 is a view similar to FIG. 7 after the balloon has been fully expanded.
Figure 9:
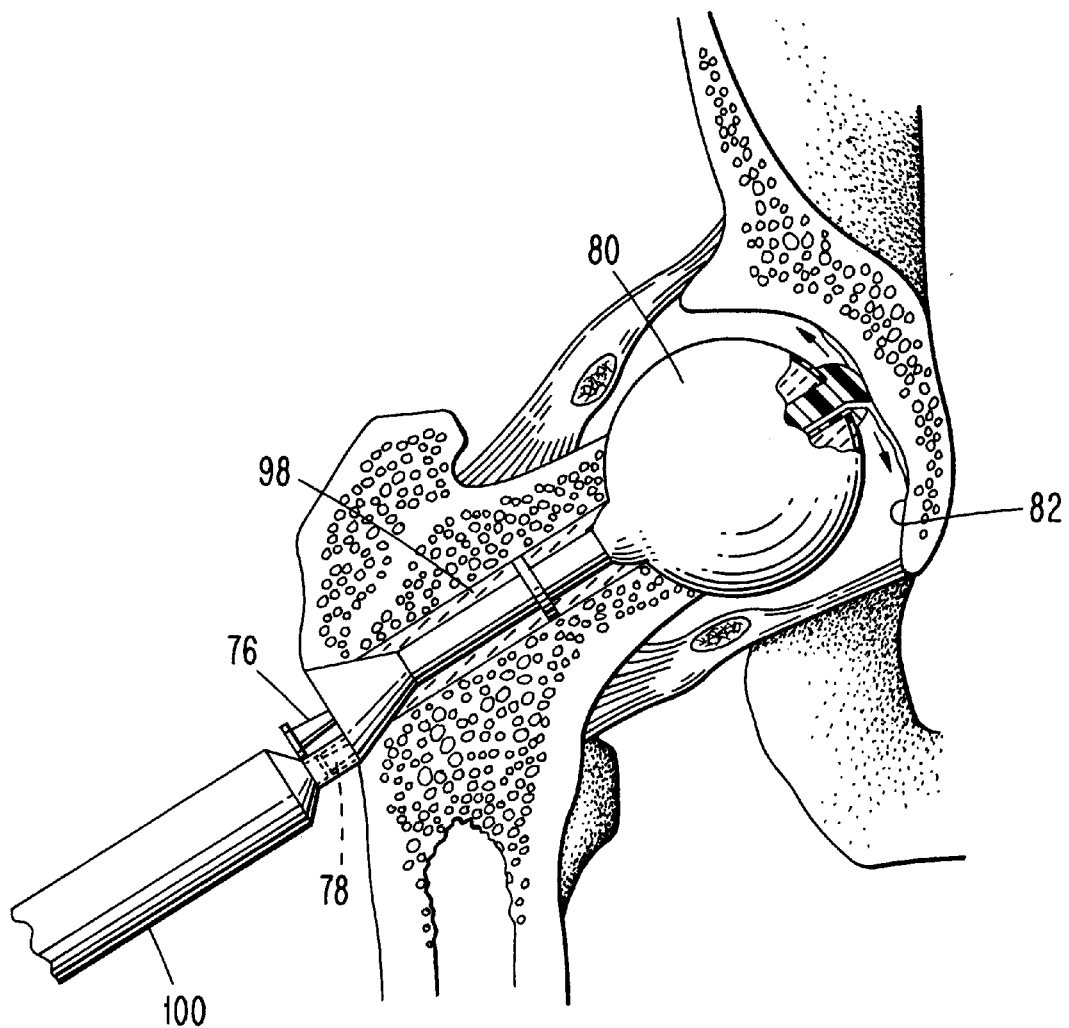
FIG. 9 is a view similar to FIG. 8 as cartilage growth-promoting cells are ejected through the molding device.

Then, as shown in FIG. 7, the barrel 90 of a syringe is fitted against the inlet port 76 that communicates with the center passage 70. The syringe barrel contains conventional fracture grout (e.g., Norian SRS) which, when the plunger 92 of the syringe is depressed, flows through the center passage 70 and the lateral passages to fill the balloon 80 and then the space 96 formed between the body 52 and the wall of the hole 31. The filling occurs in this sequence because the lateral passages 72 which exit within the balloon are of a slightly larger diameter than those that exit into space 96. This filling sequence avoids extravasation of grout into the joint space. The grout can, if necessary, flow through the through-holes 66 of the bushing 64 to allow uniform filling of space 96, thereby avoiding the formation of filling voids and potential stress risers.

Eventually, the balloon 80 forms a generally spherically cavity adjacent an end surface of the femur, and fracture grout 98 occupies the cavity and the space 96, as well as the passages 70, 72 of the body 52. The cavity formed by the balloon can be of various sizes and shapes as required, and need not be exactly spherical.

At this point, or possibly at some time later, a syringe barrel 100 is fitted to the inlet port 78 which communicates with the secondary passage 74. The syringe barrel contains the cells of the cartilage graft which were taken and stored weeks prior to the initiation of the replacement procedure. Those cells are then injected through the secondary passage 74 to fill the area between the balloon and socket in order to promote cartilage growth. The outer end of the passage 74 can then be plugged. In lieu of introducing such cells, it may be preferred instead to introduce a suitable bio-compatible resurfacing gel.

The inlet ports 76, 78 are then trimmed off the body 52 and the wound is closed in layers, with the use of a drain if needed.

It is expected that for six to eight weeks the post-operative care will involve crutch-walking so as to avoid applying weight to the replacement. Then the patient is allowed to progressively bear weight up to full weight.

Figure 10:
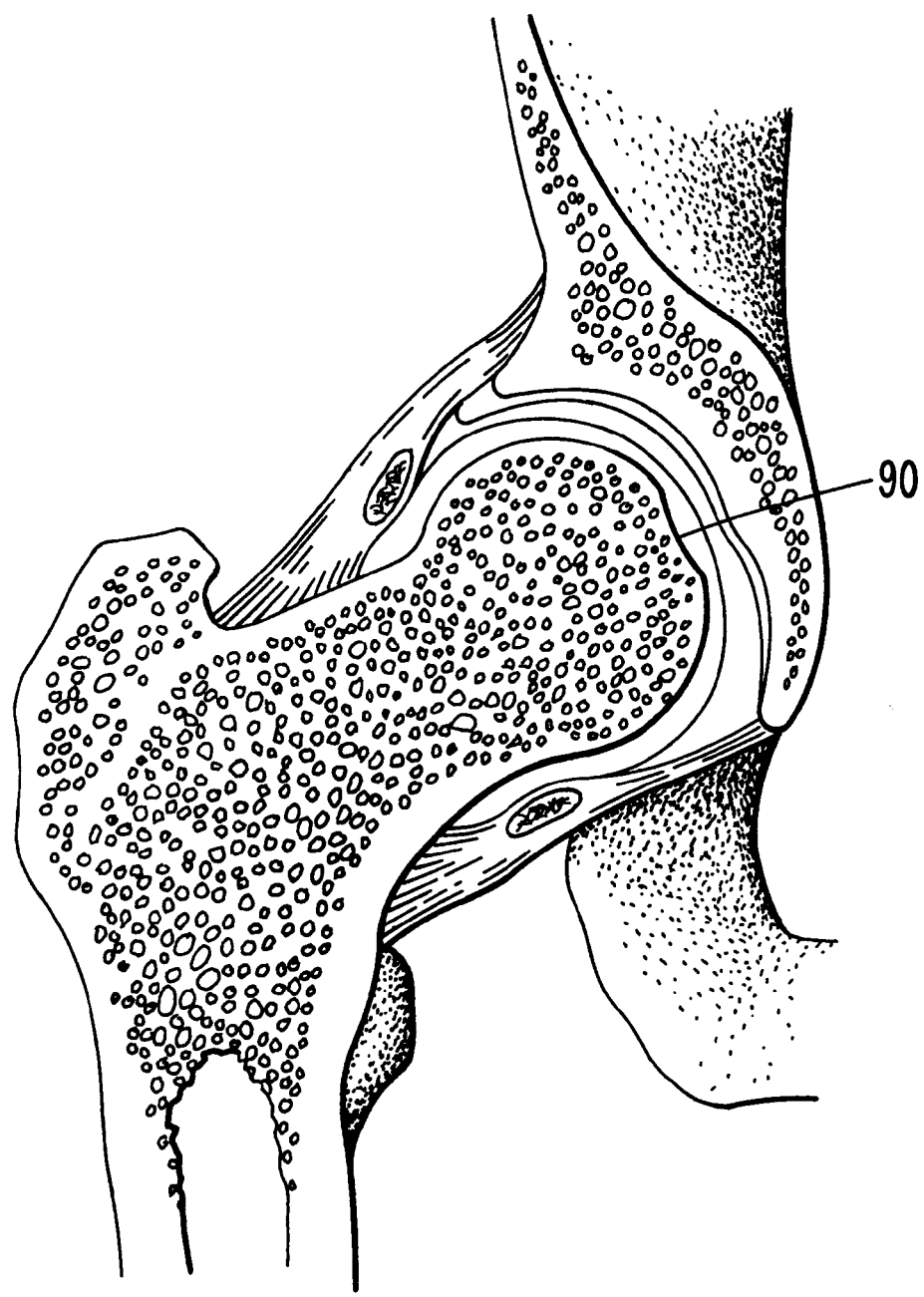
FIG. 10 is a view similar to FIG. 9 after the bioabsorbable materials of the molding device have been replaced by bone.
Figure 13:
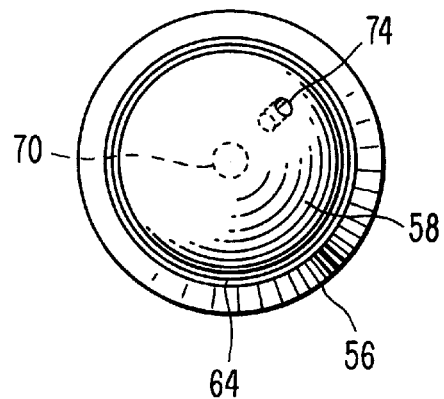
FIG. 13 is a front end view of the molding device.
Figure 14:
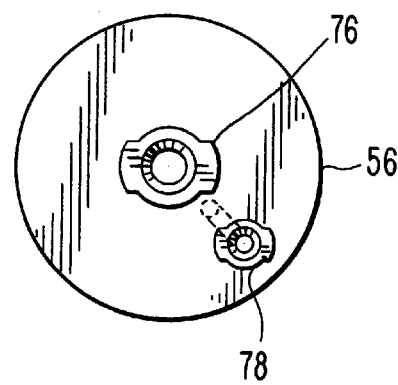
FIG. 14 is a rear end view of the molding device.
Figure 15:
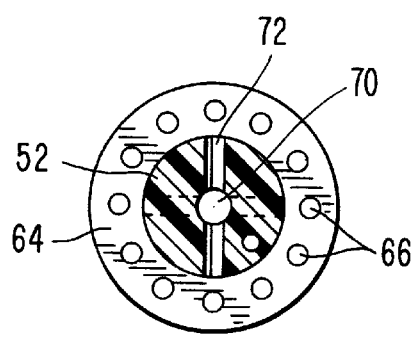
FIG. 15 is a cross-sectional view taken along the line 15—15 in FIG. 12.
Figure 16:
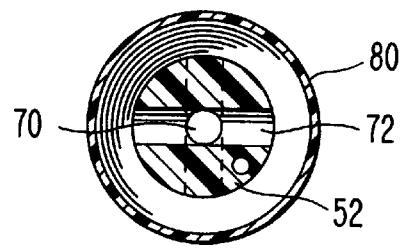
FIG. 16 is a cross-sectional view taken along the line 16—16 in FIG. 12.

FIG. 10 depicts the joint after the bioabsorbable materials of the body 52 and the balloon 80, as well as the fracture grout have been replaced by bone. The tip portion 58 of the body 52, due to its being exposed to the cartilage of the socket wall is not replaced by bone, but rather will leave an indentation 90 as the front of the neo femoral head.

Since the neo femoral head is produced through the use of bioabsorbable materials according to the invention, there remains in the socket no plastic element that can give rise to the generation of plastic particulate debris as occurs in prior art hip replacement procedures involving the use of polyethylene prostheses. Hence, no inflammation attributable to the generation of such debris can result from the procedure according to the invention. Hence, the risk of failure of the replacement should be appreciably lower when employing the present invention.

Also, a much smaller incision is required to perform a hip replacement according to the present invention, as compared with conventional techniques, so the recovery period should be shorter.

Furthermore, little blood loss would result from the procedure, thereby avoiding the need for post-operative blood transfusion as is often required in prior art procedures. Additionally, the joint capsule is preserved in the procedure of the present invention, allowing the patient to retain his/her normal hip joint position sense or proprioception.

Although the present invention has been described in connection with a preferred embodiment thereof, it will be appreciated by those skilled in the art that additions, deletions, modifications, and substitutions not specifically described may be made without departing from the spirit and scope of the invention as defined in the appended claims.

What is claimed is:

1. A hip replacement method comprising the steps of:

A) separating a femoral head from a femoral neck in a patient's body to form an end surface on the patient's femur;

B) removing the femoral head from the patient's body;

C) positioning a molding device in the patient's body for forming a cavity adjacent the end surface; and D) molding in-situ in the body a neo femoral head joined to the femoral neck by flowing a molding substance into the cavity and allowing the molding substance to harden into the shape of the neo femoral head.

2. The method according to claim 1 wherein step B comprises fragmenting the femoral head while in the body and removing the fragments from the body.

3. The method according to claim 1 including, prior to step A, the step of forming a hole through the femoral neck and the femoral head from the lateral cortex.

4. The method according to claim 3 wherein step B comprises fragmenting the severed femoral head while in the body and discharging the fragments through the hole.

5. The method according to claim 4 wherein step C comprises inserting through the hole the molding device for defining the cavity in the shape of the neo femoral head, the device formed of bioabsorbable material.

6. The method according to claim 5 wherein the molding device includes an expandable balloon, step D comprising introducing the molding substance into the balloon to expand the balloon.

7. The method according to claim 3 wherein step A comprises inserting a saw into the hole and actuating the saw to sever the femoral head from the femoral neck.

8. The method according to claim 7 wherein step C comprises inserting through the hole the molding device for defining the cavity in the shape of the neo femoral head, the device formed of bioabsorbable material.

9. The method according to claim 8 wherein the molding device includes an expandable balloon, step D comprising introducing the molding substance into the balloon to expand the balloon.

10. The method according to claim 7 wherein step B comprises fragmenting the severed femoral head while in the body and discharging the fragments through the hole.

11. The method according to claim 3 wherein step C comprises inserting through the hole the molding device for defining the cavity in the shape of the neo femoral head, the device formed of bioabsorbable material.

12. The method according to claim 11 wherein the molding device includes an expandable balloon, step D comprising introducing the molding substance into the balloon to expand the balloon.

13. The method according to claim 12 wherein step D further comprises introducing the molding substance into a passage of a body of the device on which the balloon is mounted, the molding substance conducted by the passage to a location within the balloon and to a location between the body of the device and a wall of the hole.

14. The method according to claim 1 further including, following step D, the step of introducing a cartilage-generating material into a space surrounding the neo femoral head.

15. The method according to claim 14 wherein the cartilage-generating material introduced into the space comprises cells from a cartilage graft of the patient.

16. A hip replacement method comprising the steps of:

A) inserting a guide wire through a femoral neck and femoral head from the lateral cortex of a patient;

B) drilling a hole through the femoral neck and femoral head from the lateral cortex, using the guide wire as a drill guide;

C) inserting a saw into the hole using the guide wire as a cutter guide, and severing the femoral head from the femoral neck;

D) inserting a burr into the body and reducing the femoral head to fragments while discharging the fragments through the hole;

E) inserting through the hole a molding device formed of bioabsorbable material;

F) positioning an expandable balloon of the molding device between the femoral neck and a wall of a respective hip socket;

G) introducing a molding substance through a passage of a body of the molding device and into the balloon to expand the balloon; and H) allowing the molding substance to harden.

* * * * *